(12) United States Patent
Zhuo

(10) Patent No.: US 8,124,599 B2
(45) Date of Patent: Feb. 28, 2012

(54) METHOD FOR TREATING NEURONAL AND NON-NEURONAL PAIN

(76) Inventor: Min Zhuo, Toronto (CA)

( * ) Notice: Subject to any disclaimer, the term of this patent is extended or adjusted under 35 U.S.C. 154(b) by 163 days.

(21) Appl. No.: 12/083,358

(22) PCT Filed: Oct. 13, 2006

(86) PCT No.: PCT/CA2006/001687
§ 371 (c)(1),
(2), (4) Date: Apr. 10, 2008

(87) PCT Pub. No.: WO2007/041863
PCT Pub. Date: Apr. 19, 2007

(65) Prior Publication Data
US 2009/0233922 A1    Sep. 17, 2009

Related U.S. Application Data

(60) Provisional application No. 60/726,718, filed on Oct. 14, 2005.

(51) Int. Cl.
*A61K 31/33* (2006.01)
(52) U.S. Cl. ........................................ 514/183
(58) Field of Classification Search .................. 514/183
See application file for complete search history.

(56) References Cited

U.S. PATENT DOCUMENTS

| | | | |
|---|---|---|---|
| 2,691,654 A | 10/1954 | Hitchings et al. | |
| 2,844,577 A | 7/1958 | Acker | |
| 4,189,485 A | 2/1980 | Matsuno et al. | |
| 2004/0013669 A1 | 1/2004 | Wei et al. | |

FOREIGN PATENT DOCUMENTS

| EP | 191561 | | 8/1986 |
|---|---|---|---|
| EP | 06790842.6 | | 7/2008 |
| JP | 54055733 A | * | 5/1979 |
| RU | 2233842 | | 8/2004 |
| WO | WO 02/055521 | | 7/2002 |
| WO | WO 03/104482 | | 12/2003 |
| WO | WO 2004/037159 | | 5/2004 |
| WO | WO 2004/078183 A1 | * | 9/2004 |
| WO | WO 2005/084653 | | 9/2005 |
| WO | WO 2005/092306 | | 10/2005 |
| WO | WO 2006/002422 | | 1/2006 |

OTHER PUBLICATIONS

English Translation of JP54055733A.*
Anderson, et al., (2000) Phosphorylated cAMP response element binding protein increases in neurokinin-1 receptor-immunoreactive neurons in rat spinal cord in response to formalin-induced nociception. Neurosci Lett 283:29-32.
Haley et al., (1990) Peripheral kappa-opioid modulation of the formalin response: an electrophysiological study in the rat. Eur J Pharmacol 19-1:437-446.
Kandel ER (2001) The molecular biology of memory storage: a dialogue between genes and synapses. Science 294:1030-1038.
Kawasaki et al., (2004) Ionotropic and metabotropic receptors, protein kinase A, protein kinase C, and Src contribute to C-fiber-induced ERK activation and cAMP response element-binding protein phosphorylation in dorsal horn neurons, leading to central sensitization. J Neurosci 24:8310-8321.
Ko et al., (2005) Selective contribution of Egyl (zif/268) to persistent inflammatory pain. J Pain 6:12-20.
Li et al., (2004) Alterations in spinal cord gene expression after hindpaw formalin injection. J Neurosci Res 78:533-541.
Nestler EJ (2001) Molecular basis of long-term plasticity underlying addiction. Nat Rev Neurosci 2:119-128.
Sluka et al., (2001) Unilateral intramuscular injections of AC1dic saline produce a bilateral, long-lasting hyperalgesia. Muscle Nerve 24:37-46.
Wei et al., (2000) Role of EGR1 in hippocampal synaptic enhancement induced by tetanic stimulation and amputation. J Cell Biol 149:1325-1334.
Wei et al., (2001) Genetic enhancement of inflammatory pain by forebrain NR2B overexpression. Nat Neurosci 4:164-169.
Wei et al., (2002a) Calcium calmodulin-dependent protein kinase IV is required for fear memory. Nat Neurosci 5:573-579.
Wei et al., (2002b) Genetic elimination of behavioral sensitization in mice lacking calmodulin-stimulated adenylyl cyclases. Neuron 36:713-726.
Wong et al., (1999) Calcium-stimulated adenylyl cyclase activity is critical for hippocampus-dependent long-term memory and late phase LTP. Neuron 23:787-798.
Woolf et al., (2000) Neuronal plasticity: increasing the gain in pain. Science 288:1765-1769.
Wu et al. (1995) Altered behavior and long-term potentiation in type I adenylyl cyclase mutant mice. Proc Natl Acad Sci U S A 92:220-224.
Xia et al., (1997) Calmodulin-regulated adenylyl cyclases and neuromodulation. Curr Opin Neurobiol 7:391-396.
Zhuo M (2004) Central plasticity in pathological pain. Novartis Found Symp 261:132-145; discussion 145-154.
Khasar et al., (1999) Epinephrine Produces a b-Adrenergic Receptor-Mediated Mechanical Hyperalgesia and In Vitro Sensitization of Rat Nociceptors, J Neurophysiol 81:1104-1112.
Khasar et al., (1995) Mu-opioid agonist enhancement of prostaglandin-induced hyperalgesia in the rat: A G-protein β? subunit-mediated effect? Neuroscience vol. 67, Issue 1, Jul. 1995, pp. 189-195 (Abstract only).
Hoeger et al., "The role of the cAMP pathway in a chronic muscle pain model in rats" Society for Neuroscience Abstracts, vol. 25, No. 2, 2001, p. 2168, XP009119832.
Wei F et al: "Reduced inflammatory pain and preserved acute pain in mice lacking calmodulin stimulated adenylyl cyclases" Abstracts of the Annual Meeting of the Society for Neuroscience, Society for Neuroscience, Washington, DC, US, vol. 27, No. 1, Nov. 10, 2001, p. 144.

* cited by examiner

*Primary Examiner* — Brandon Fetterolf
*Assistant Examiner* — Christopher R Stone

(57) ABSTRACT

A method for the combined treatment of neuronal and non-neuronal pain in mammals is provided comprising administration of adenylyl cyclase 1 inhibitors having the following general formula (1): (1) wherein: G, H, J and M are each N, or H and J are each C, and G and M are each N, S or O, or H, J and M are each C and G is N, S or O.

3 Claims, 11 Drawing Sheets

BTB 14111

HTS 09836

HTS 11215

HTS 11216

HTS 11457

JFD 02793

RJC 03312

SQ 22536

BAS 03384370

BAS 01118261

CD 4786-0073

METHOD FOR TREATING NEURONAL AND NON-NEURONAL PAIN

FIELD OF THE INVENTION

The present invention relates to the treatment of pain. In particular, the invention relates to a novel method for the combined treatment of both neural and non-neural pain by modulating adenylcyclase 1 (AC1) activity, and compositions useful therefore.

BACKGROUND OF THE INVENTION

Neuropathic pain and inflammatory pain differ in their etiology, pathophysiology and responses to treatment with different pharmaco-therapeutical agents. Injuries usually lead to a combination of both types of pain due to the involvement of both nerve fibers and accompanying inflammation. Most of the time one component might dominate over the other making a definitive diagnosis difficult. Moreover, the present treatment modalities for these two types of pain are entirely different making it difficult to completely alleviate the pain by one treatment. Severe acute pain responds to μ opioid receptor agonists (morphine) and NMDA receptor antagonists (ketamine); chronic inflammatory pain responds to cycloxygenase inhibitors (Bextra™, Celebrex™) and prostaglandin inhibitors (acetaminophen); neuropathic pain responds to antiepileptic medications (carbamazepine) and drugs of still not completely known actions (gabapentin).

Pain induces elevated levels of molecules downstream of adenylyl cyclases in neuronal populations, in dorsal root ganglion neurons, spinal dorsal horn and anterior cingulate cortex (ACC) that are activated in pain transmission. These molecules include transcription factor pCREB (Anderson and Seybold, 2000; Kawasaki et al., 2004, Ma and Quirion, 2001) and immediate early genes Egr-1 (Wei et al., 2000, Ko et al., 2005) and Arc (Li et al., 2004). Adenylyl cyclases (ACs) are known as coincidence detectors in neurons due to their specific interaction with G-proteins, NMDA receptors, voltage-dependent calcium channels and μ opioid receptors at the neuronal membrane. The role of adenylyl cyclases was shown to be important in behavioral sensitization associated with chronic inflammation (Wei et al., 2002b). Common signaling pathways induced by the activation of adenylyl cyclases have demonstrated their capability as key initiator molecules in memory and inflammatory pain (Woolf and Salter, 2000); (Kandel, 2001, Nestler, 2001 and Zhuo, 2004) and their contribution to NMDA receptor-dependent synaptic potentiation lasting several hours (Wong et al., 1999).

Of the ten different isoforms of ACs that have been identified (Xia and Storm, 1997), AC1 is a calcium calmodulin (CaM)-stimulated AC present in the brain and spinal cord which is highly neuron-specific. Mice lacking AC1 and 8 were shown to lack long term memory for passive avoidance, contextual and spatial memory ((Wong et al., 1999, Wu et al., 1995). Mice lacking AC1 and 8 also showed reduced chronic inflammatory pain in mice (Wei et al., 2002b). Thus, the neuronal membrane bound ACs are important membrane-bound enzymes that can modulate the downstream cascade of molecules that eventually regulate gene transcription and mediate their effect through the expressed proteins either in nerve conduction or in synaptic plasticity changes. A comparative study of the effect of AC1 and AC8 was conducted to identify the more effective isoform to target. Mice lacking AC1 were found to have a superior effect on subcutaneous inflammatory pain (Wei et al, 2002), acute muscle pain, chronic muscle pain and neuropathic pain.

Given the foregoing, it would be desirable to develop a protocol that down-regulates AC1 to yield a treatment which targets pain of both neural and non-neural origin.

SUMMARY OF THE INVENTION

It has now been found that adenylyl cyclase inhibitors belonging to a family of cyclic compounds is useful in the combined, simultaneous treatment of both neural and non-neural pain.

Thus, in one aspect of the invention, a method is provided for the combined treatment of neural and non-neural pain in a mammal. The method comprises the step of administering a therapeutically effective amount of a compound having the following general formula (1):

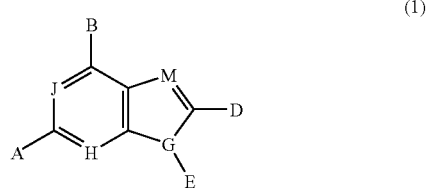

(1)

wherein:

A is selected from the group consisting of H, OH, halogen, $C_1$-$C_6$ alkyl, $C_1$-$C_6$ alkyl halide, $C_2$-$C_6$ alkenyl, $C_2$-$C_6$ alkynyl and $C_1$-$C_6$ alkoxy;

B is selected from the group consisting of:
hydroxy, thio, —$OR^1$, —$NH_2$, —$NO_2$, —$NHR^1$, —$NR^1R^2$, —$SR^1$ or —$C_1$-$C_6$ saturated or unsaturated alkyl group optionally substituted with one or more substituents selected from hydroxy, halogen, thio, $OR^1$, $NH_2$, $NO_2$, $NHR^1$, $NR^1R^2$, $SR^1$, a $C_3$-$C_{10}$ aromatic or non-aromatic ring structure or a $C_3$-$C_9$ aromatic or non-aromatic heterocyclic ring structure optionally substituted with OH, halogen, thio, $NH_2$, $C_1$-$C_6$ alkyl, $C_1$-$C_6$ alkanol or $C_1$-$C_6$ alkoxy, wherein $R^1$ and $R^2$ are independently selected from the group consisting of $C_1$-$C_6$ alkyl, $C_1$-$C_6$ alkanol, $C_1$-$C_6$ alkoxy and $C_1$-$C_6$ carboxyalkyl, or $NR^1R^2$ forms a $C_3$-$C_6$ aromatic or non-aromatic heterocyclic ring optionally substituted with OH, halogen, thio, $NH_2$, $NO_2$, $C_1$-$C_6$ alkyl, $C_1$-$C_6$ alkanol, $C_1$-$C_6$ alkoxy or $C_1$-$C_6$ carboxyalkyl, D is selected from the group consisting of:
H, halogen, hydroxy, $NH_2$, thio, $NHR^1$, $NR^1R^3$, $SR^1$, $C_1$-$C_6$ alkyl, $C_1$-$C_6$ alkoxy, wherein $R^1$ is as defined above and $R^3$ is as defined for $R^1$;

E is H or OH, or
$C_1$-$C_6$ alkyl, $C_1$-$C_6$ alkoxy, $C_{3-10}$-aryl-$C_{1-6}$-alkyl or $C_{3-10}$-aryloxy-$C_{1-6}$-alkyl optionally substituted with $C_{1-6}$-alkyl, amino, $NHR^1$, $NR^1R^2$, thio, $SR^1$, an unsubstituted $C_3$-$C_7$ cycloalkyl, phenyl or $C_4$-$C_6$ heterocyclic ring, or a substituted $C_3$-$C_7$ cycloalkyl, phenyl or $C_4$-$C_6$ heterocyclic ring having one or more substituents selected from the group consisting of $C_1$-$C_6$ alkyl, $C_1$-$C_6$ alkoxy, $C_1$-$C_6$ alkanoyl, $C_1$-$C_6$ carboxyalkyl, halogen or OH, or an unsubstituted $C_3$-$C_7$ cycloalkyl, phenyl or $C_4$-$C_6$ heterocyclic ring, or a substituted $C_3$-$C_7$ cycloalkyl, phenyl or $C_4$-$C_6$ heterocyclic ring having one or more substituents selected from the groups consisting of $C_1$-$C_6$ alkyl, $C_1$-$C_6$ alkoxy, $C_1$-$C_6$ alkanoyl, $C_1$-$C_6$ carboxyalkyl, halogen or OH, wherein $R^1$ and $R^2$ are as defined above; and
G, H, J and M are each N, or
H and J are each C, and G and M are each N, S or O, or
H, J and M are each C and G is N, S or O.

In another aspect of the invention, a composition is provided for the combined treatment of neuronal and non-neuronal pain. The composition comprises a compound of formula (1) as set out above in combination with a pharmaceutically acceptable carrier.

In another aspect, an article of manufacture is provided. The article of manufacture comprises packaging material containing a composition. The composition comprises a compound of formula (1) and a pharmaceutically acceptable carrier. The packaging material is labeled to indicate that the composition is useful in the combined treatment of both neural and non-neural pain in a mammal.

In another aspect of the present invention, use of a compound as defined by formula (1) is provided for therapy.

In a further aspect, use of a compound as defined by formula (1) is provided for the manufacture of a medicament for the combined treatment of neural and non-neural pain.

These and other aspects of the invention are described by reference to the following figures in which:

DETAILED DESCRIPTION OF THE INVENTION

Figure 1:
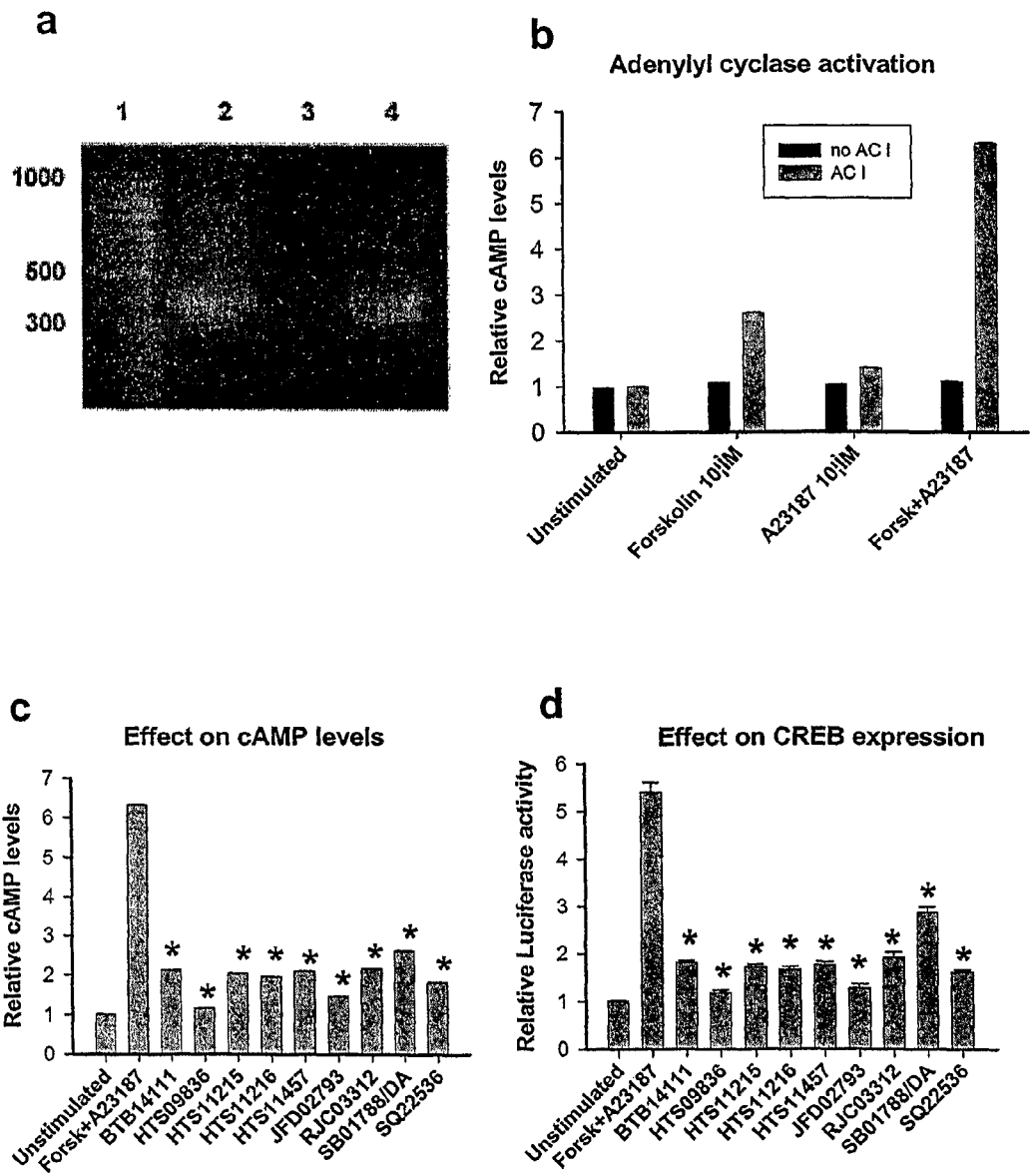
FIG. 1a illustrates the stable transfection of AC1 expression vectors into HEK cell lines as confirmed by RT-PCR amplification.
FIG. 1b graphically illustrates forskolin and calcium ionophore stimulation on adenylyl cyclase1 in AC1 transfected cell lines. Data are expressed relative to unstimulated cAMP level of AC I expression HEK293 cells (n=4 cells)
FIG. 1c graphically illustrates the effect of non-competitive AC1 inhibitors on forskolin and calcium ionophore stimulation of adenylyl cyclase.
FIG. 1d graphically illustrates the effect of non-competitive AC1 inhibitors on adenylyl cyclase1 shown as changes in CREB expression levels.

The present invention provides a method in which inhibitors of AC1 are used in the combined treatment of neural and non-neural pain in a mammal. The method advantageously has little or no effect on acute pain and general behaviours such as motor function, heart rate and anxiety.

The term "combined treatment" refers to the simultaneous treatment of two different types of pain, namely, pain of neural origin (neuropathic pain) and pain of non-neural origin (nociceptive pain) at the same time by a single therapy, e.g. the administration of an AC1 inhibitor defined by formula (1). For clarity, "treatment" refers to the reduction, at least in part, of neural and non-neural pain by some degree of inhibition of AC1, including the partial inhibition thereof.

The term "mammal" as it is used herein is meant to encompass humans as well as non-human mammals such as domestic animals (e.g. dogs, cats and horses), livestock (e.g. cattle, pigs, goats, sheep) and wild animals.

Neural or neuropathic pain refers to pain resulting from an injury to or malfunction in the peripheral or central nervous system. Neural pain may be triggered by an injury, but does not necessarily involve actual damage to the nervous system. Nerves can be infiltrated or compressed by tumors, strangulated by scar tissue, or inflamed by infection. Neuropathic pain is frequently chronic, and does not respond well to treatment with opioids. Examples of neuropathic pain include, but are not limited to, lower back pain, migraine and headache, and pain resulting from a disease state such as any type of cancer or a disease associated with the immune system.

Non-neural or nociceptive pain refers to pain from tissue injury, including for example, sprains, bone fractures, burns, bumps, bruises, inflammation, obstructions and myofascial pain. This type of pain is usually time-limited (as opposed to chronic) and responds well to opioid treatment.

In one aspect of the present invention, a method comprising the simultaneous treatment of both neural and non-neural pain in a mammal is provided. In this method, neural and non-neural pain is treated by inhibition of AC1 using inhibitors having the following general formula (1):

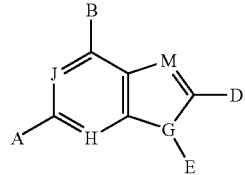

(1)

wherein:
A is selected from the group consisting of H, OH, halogen, $C_1$-$C_6$ alkyl, $C_1$-$C_6$ alkyl halide, $C_2$-$C_6$ alkenyl, $C_2$-$C_6$ alkynyl and $C_1$-$C_6$ alkoxy;

B is selected from the group consisting of:
hydroxy, thio, —$OR^1$, —$NH_2$, —$NO_2$, —$NHR^1$, —$NR^1R^2$, —$SR^1$ or —$C_1$-$C_6$ saturated or unsaturated alkyl group optionally substituted with one or more substituents selected from hydroxy, halogen, thio, $OR^1$, $NH_2$, $NO_2$, $NHR^1$, $NR^1R^2$, $SR^1$, a $C_3$-$C_{10}$ aromatic or non-aromatic ring structure or a $C_3$-$C_9$ aromatic or non-aromatic heterocyclic ring structure optionally substituted with OH, halogen, thio, $NH_2$, $C_1$-$C_6$ alkyl, $C_1$-$C_6$ alkanol or $C_1$-$C_6$ alkoxy, wherein $R^1$ and $R^2$ are independently selected from the group consisting of $C_1$-$C_6$ alkyl, $C_1$-$C_6$ alkanol, $C_1$-$C_6$ alkoxy and $C_1$-$C_6$ carboxyalkyl, or $NR^1R^2$ forms a $C_3$-$C_6$ aromatic or non-aromatic heterocyclic ring optionally substituted with OH, halogen, thio, $NH_2$, $NO_2$, $C_1$-$C_6$ alkyl, $C_1$-$C_6$ alkanol, $C_1$-$C_6$ alkoxy or $C_1$-$C_6$ carboxyalkyl;

D is selected from the group consisting of:
H, halogen, hydroxy, $NH_2$, thio, $NHR^1$, $NR^1R^3$, $SR^1$, $C_1$-$C_6$ alkyl, $C_1$-$C_6$ alkoxy, wherein $R^1$ is as defined above and $R^3$ is as defined for $R^1$;

E is H or OH, or $C_1$-$C_6$ alkyl, $C_1$-$C_6$ alkoxy, $C_{3-10}$-aryl-$C_{1-6}$-alkyl or $C_{3-10}$-aryloxy-$C_{1-6}$-alkyl, optionally substituted with $C_{1-6}$-alkyl, amino, $NHR^1$, $NR^1R^2$, thio, $SR^1$, an unsubstituted $C_3$-$C_7$ cycloalkyl, phenyl or $C_4$-$C_6$ heterocyclic ring, or a substituted $C_3$-$C_7$ cycloalkyl, phenyl or $C_4$-$C_6$ heterocyclic ring having one or more substituents selected from the group consisting of $C_1$-$C_6$ alkyl, $C_1$-$C_6$ alkoxy, $C_1$-$C_6$ alkanoyl, $C_1$-$C_6$ carboxyalkyl, halogen or OH, or an unsubstituted $C_3$-$C_7$ cycloalkyl, phenyl or $C_4$-$C_6$ heterocyclic ring, or a substituted $C_3$-$C_7$ cycloalkyl, phenyl or $C_4$-$C_6$ heterocyclic ring having one or more substituents selected from the group consisting of $C_1$-$C_6$ alkyl, $C_1$-$C_6$ alkoxy, $C_1$-$C_6$ alkanoyl, $C_1$-$C_6$ carboxyalkyl, halogen or OH, wherein $R^1$ and $R^2$ are as defined above; and G, H, J and M are each N, or H and J are each C, and G and M are each N, S or O, or H, J and M are each C and G is N, S or O.

The base heterocyclic ring system in the compound of formula (1) may be such that each of variables G, H, J and M are nitrogen (N), i.e. a purine ring system. Alternatively, H and J may each be carbon, and G and M may be selected from N, S or O, for example, benzothiazole. In another alternative, H, J and M may each be carbon (C) and G may be either N, S or O, e.g. to yield an indole, benzothiophene or benzofuran ring system, respectively.

The variable A may be H; OH; halogen such as F, Cl, Br and I; $C_1$-$C_6$ alkyl, including branched alkyl groups, such as methyl, ethyl, propyl, isopropyl, butyl, isobutyl, sec-butyl, tert-butyl, pentyl, isopentyl, 3-methylpentyl, hexyl and iso-hexyl; $C_1$-$C_6$ alkyl halide such as chloromethyl, fluoromethyl, bromoethyl, bromoethylenyl, propylfluoro, isopropyliodo, chlorobutyl, 1,1-dichloro-2,3-butyl, 2-bromopentyl, 3-chlorohexyl, 1-fluoro-3-methylhexyl and 1,1-difluorohexyl; $C_2$-$C_6$ alkenyl, including branched alkenyl groups, for example, ethylenyl, propylenyl, butenyl, isobutenyl, 2-butenyl, pentenyl, isopentenyl, 2-pentenyl and hexenyl; $C_2$-$C_6$ alkynyl such as ethynyl, propynyl and butynyl, including branched alkynyl groups; $C_1$-$C_6$ alkoxy, including branched alkoxy groups, such as methoxy, ethoxy, propyloxy, isopropyloxy, butyloxy, isobutyloxy, methoxymethyl, ethoxymethyl, ethoxyethyl, methoxyethyl, methoxypropyl, ethoxypropyl, propyloxymethyl, propyloxyethyl, propyloxypropyl, pentyloxy, isopentyloxy, hexyloxy and isohexyloxy.

The variable B may be hydroxy, halogen, thio, —$OR^1$, —$NH_2$, —$NO_2$, —$NHR^1$, —$NR^1R^2$, $SR^1$, or —$C_1$-$C_6$ saturated or unsaturated alkyl group, for example, alkyl, alkenyl or alkynyl groups as exemplified above, optionally substituted with one or more substituents selected from hydroxy, halogen, thio, —$OR^1$, —$NH_2$, —$NO_2$, —$NHR^1$, —$NR^1R^2$ or —$SR^1$, or a $C_3$-$C_{10}$ aromatic or non-aromatic ring structure or a $C_3$-$C_9$ aromatic or non-aromatic heterocyclic ring structure optionally substituted with OH, halogen, thio, $NH_2$, $C_1$-$C_6$ alkyl, $C_1$-$C_6$ alkanol or $C_1$-$C_6$ alkoxy. The term "ring structure" is used herein to refer to structures comprised of a single ring as well as multi-cyclic structures, such as bicyclic structures. The term "heterocyclic ring" or "heterocyclic ring structure" is meant to include 3-9-membered ring structures that include at least one hetero atom selected from O, S and N within the core ring structure. Examples of suitable ring structures include benzene, naphthalene, tetralin, decalin, piperidine, pyrrolidine, furan, piperazine, tetrahydrothiphene, morpholine, imidazole, benzothiophene, quinoline, isoquinoline, indole, benzofuran and purine.

The variables $R^1$ and $R^2$ are independently selected from the group consisting of $C_1$-$C_6$ alkyl, $C_1$-$C_6$ alkyl halide, $C_1$-$C_6$ alkenyl, $C_1$-$C_6$ alkynyl, $C_1$-$C_6$ alkanol, $C_1$-$C_6$ alkoxy, or $C_1$-$C_6$ carboxyalkyl. Thus, $OR^1$ may be, for example, oxymethyl, oxy-dimethyl, oxyethyl, oxy-3-chlorobutyl, oxypropylenyl, or oxypropanol. $NHR^1$ may be, for example, alkylamine such as methylamine, as well as 2-chloropropylamine, NH-ethanol, NH-propanol, NH-ethylmethyl ether or N-butyric acid. Similarly, $NR^1R^2$ may be a dialkylamine such as di-ethylamine, or may be, for example, N-chloro-N-propyl, N-methyl-N-butyric acid, N-methyl-N-propanol.

$NR^1R^2$ may also form a $C_3$-$C_{10}$ aromatic or non-aromatic heterocyclic ring structure, as exemplified above, that may optionally be substituted with OH, halogen, thio, $NH_2$, $NO_2$, $C_1$-$C_6$ alkyl, $C_1$-$C_6$ alkanol, $C_1$-$C_6$ alkoxy or $C_1$-$C_6$ carboxyalkyl.

The variable D may be H, halogen, hydroxy, $NH_2$, thio, —$NHR^1$, —$NR^1R^3$, —$SR^1$, —$C_1$-$C_6$ alkyl or —$C_1$-$C_6$ alkoxy. $R^1$ is as defined above and $R^3$ is as defined for $R^1$. Thus, D may be, for example, an unsubstituted group such as H, halogen, hydroxy, —$NH_2$, thio (S), —$C_1$-$C_6$ alkyl or —$C_1$-$C_6$ alkoxy. D may also be a substituted group, for example, D may be —$NHR^1$ in which $R^1$ is a $C_1$-$C_6$ alkyl such as methyl, ethyl, isopropyl, butyl, isobutyl, pentyl, 2-methyl-butyl; D may be —$NR^1R^3$ such as methylethyl amine or N-propyl-N-bromoamine; or D may be —$SR^1$ such as thioethyl, thiopentyl, thio-ethanoic acid. $C_1$-$C_6$ alkyl and $C_1$-$C_6$ alkoxy may also optionally be substituted with halogen, hydroxy, $NH_2$, thio, $NHR^1$, $NR^1R^3$ and $SR^1$ as previously described.

The variable E may be H or OH. E may also be $C_1$-$C_6$ alkyl, $C_1$-$C_6$ alkoxy, $C_{3-10}$-aryl-$C_{1-6}$-alkyl or $C_{3-10}$-aryloxy-$C_{1-6}$-alkyl optionally substituted with $C_{1-6}$-alkyl, amino, —$NHR^1$, —$NR^1R^2$, thio, —$SR^1$, an unsubstituted $C_3$-$C_7$ cycloalkyl, phenyl or $C_4$-$C_6$ heterocyclic ring, or a substituted $C_3$-$C_7$ cycloalkyl, phenyl or $C_4$-$C_6$ heterocyclic ring having one or more substituents selected from the group consisting of $C_1$-$C_6$ alkyl, $C_1$-$C_6$ alkoxy, $C_1$-$C_6$ alkanoyl, $C_1$-$C_6$ carboxyalkyl, halogen and OH. E may also be an unsubstituted $C_3$-$C_7$ cycloalkyl, benzyl or $C_4$-$C_6$ heterocyclic ring, or a substituted $C_3$-$C_7$ cycloalkyl, benzyl or $C_4$-$C_6$ heterocyclic ring having one or more substituents selected from the group consisting of $C_1$-$C_6$ alkyl, $C_1$-$C_6$ alkoxy, $C_1$-$C_6$ alkanoyl, $C_1$-$C_6$ carboxyalkyl, halogen and OH. $R^1$ and $R^2$ are as previously defined.

Specific examples of groups that E may be include -methylphenyl, -ethylphenyl, -propylphenyl, -methylamine-phenyl, -methylamine-propanol, -ethylamine-pentanol, -1-methyl-2,6-dichlorophenyl, -1-2,3-dihydroxy-4-methan-ol-tetrahydrofuran and -p-ethoxy-tolyl.

To determine whether a compound of formula (1) inhibits AC1, well-established assays may be used such as the cAMP assay. Since AC1 catalyzes the conversion of ATP to cAMP, production of cAMP by AC1-expressing cells in the presence of a test compound can be monitored to determine the AC1 inhibitory activity of the test compound. Briefly, non-AC1-expressing cells transfected with DNA encoding AC1 are incubated with varying concentrations of a potential AC1-inhibiting compound. Following a suitable reaction time, AC1 activity is measured by determining the amount of cAMP in the reaction mixture. Little or no cAMP is indicative of inhibitory activity.

A dual luciferase reporter system may also be used to determine AC1 inhibitory activity, as described in more detail in the specific examples that follow. In this assay, changes in intracellular cAMP concentration are detected as changes in expression level of firefly luciferase, the transcription of which is regulated by the transcription factor cAMP response element binding protein (CREB) binding to upstream cAMP response element (CRE). Cells, such as HEK293 cells, are transfected with luciferase-encoding constructs and incubated with a test compound Following a suitable incubation period, luciferase activity is determined. Inhibition of luciferase activity is indicative of an AC1 inhibitor.

Figure 6:
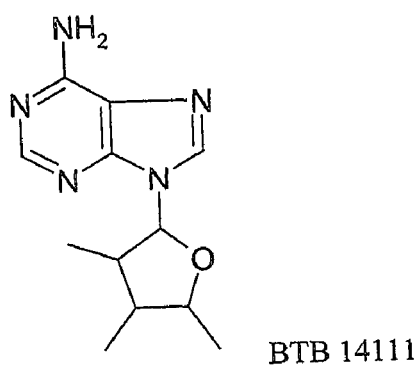
FIG. 6 illustrates exemplary AC1 inhibitors in accordance with the invention.
Figure 6:
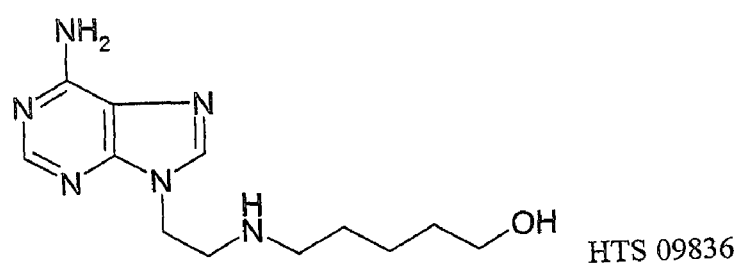
Figure 6:
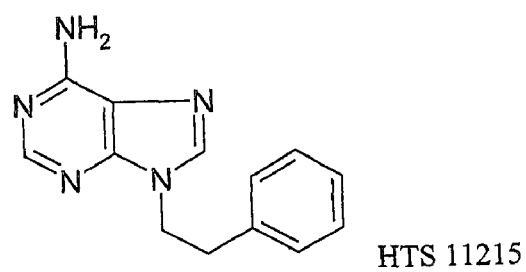
Figure 6:
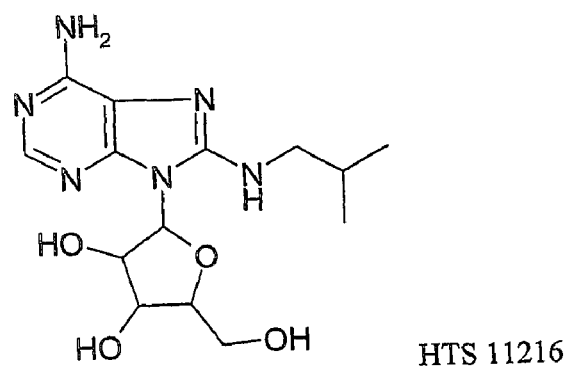
Figure 6:
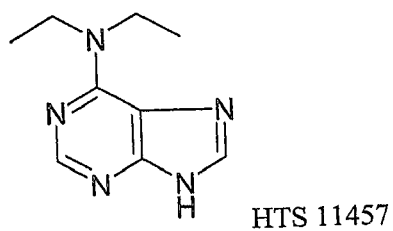
Figure 6:
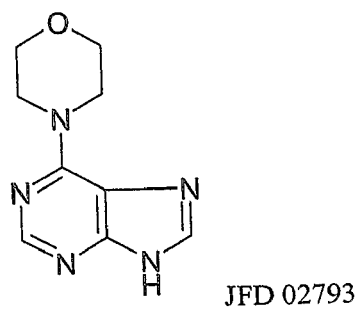
Figure 6:
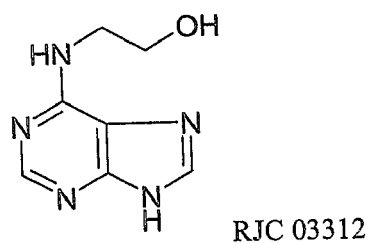
Figure 6:
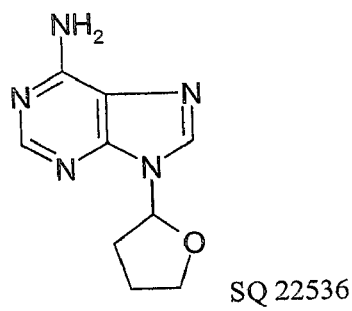
Figure 6:
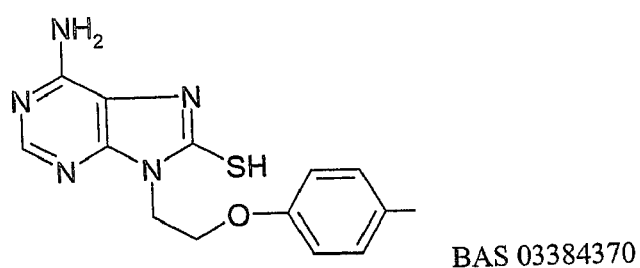
Figure 6:
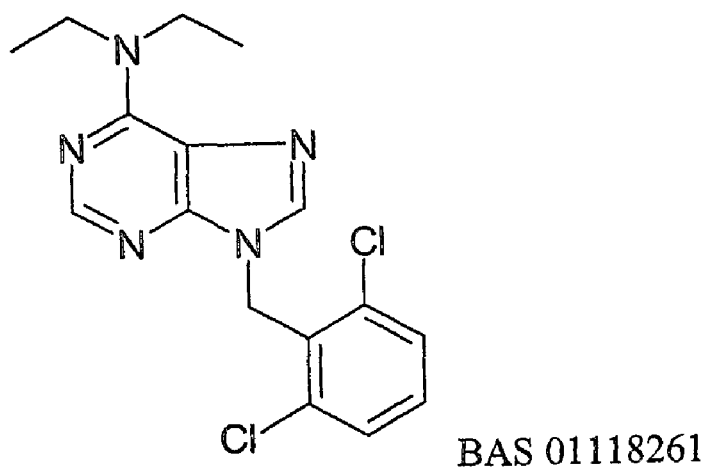
Figure 6:
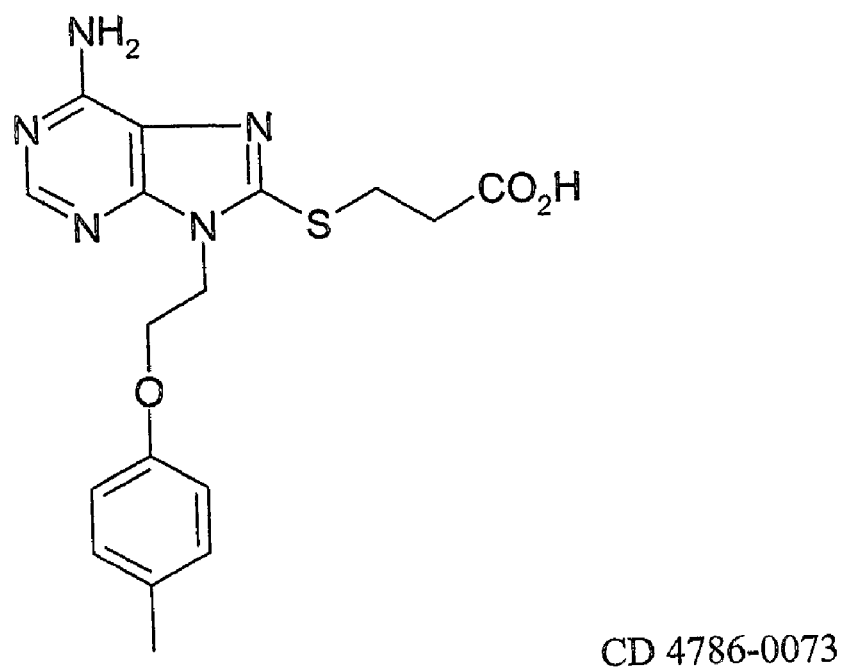

Examples of compounds in accordance with formula (1) include those compounds illustrated in FIG. 6. Although these compounds can readily be synthesized using standard chemical synthesis protocols, as one of skill in the art would appreciate, they may also be purchased from suppliers such as Asinex Ltd., Chemical Diversity Labs and Maybridge. Specifically, compounds denoted "BAS" herein may be purchased from Asinex Ltd., compounds denoted "HTS", "JFD", "RJC", "SB" and "BTB" may be purchased from Maybridge and compounds denoted "C" may be purchased from Chemical Diversity Labs.

In another aspect of the present invention, a method comprising the simultaneous treatment of both neural and non-neural pain is provided using purine inhibitors having the following general formula (2):

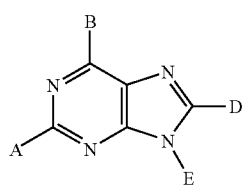

(2)

wherein variables A, B, D and E are as defined above.

Methods of treatment in accordance with the invention include the administration and/or use of AC1 inhibitors as defined above generally in the form of a pharmaceutical composition. Pharmaceutical compositions in accordance with the invention typically include the AC1 inhibitor and a pharmaceutically acceptable carrier. Pharmaceutically acceptable carriers can be selected to be suitable for the desired route of administration. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, intraperitoneal, parenteral, spinal or epidermal administration (e.g., by injection or infusion). Depending on the route of administration, the active compound, i.e. AC1 inhibitor, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M. et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain, for example, preservatives, wetting agents, emulsifying agents, flavouring agents and/or dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Therapeutic compositions typically must be sterile and stable under the conditions of manufacture and storage. Sterile injectable solutions can be prepared by incorporating the active compound in the required amount in an appropriate solvent with one or a combination of ingredients enumerated above, as required, followed by sterilization microfiltration. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

The amount of active ingredient which can be combined with a carrier material to produce a single dosage form will vary depending upon the mammal being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammal to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A "therapeutically effective dosage" of the AC1 inhibitor of the invention preferably results in decreased neural and non-neural (e.g. inflammatory) pain. One of ordinary skill in the art would be able to determine such amounts based on such factors as the mammalian patient's size, the severity of symptoms, and the particular composition or route of administration selected.

For administration of the AC1 inhibitor to a mammal, the dosage typically ranges from about 0.0001 to 100 mg/kg, and more usually 0.01 to 5 mg/kg, of body weight. For example dosages can be 0.3 mg/kg body weight, 1 mg/kg body weight, 3 mg/kg body weight, 5 mg/kg body weight or 10 mg/kg body weight or within the range of 0.1-10 mg/kg.

A composition of the present invention can be administered via one or more routes of administration using one or more of a variety of methods known in the art. As will be appreciated by the skilled artisan, the route and/or mode of administration will vary depending upon the desired results. Preferred routes of administration for the AC1 inhibitors of the invention include parental routes, including intravenous, intramuscular, intradermal, intraperitoneal, subcutaneous, spinal, intraarterial, intrathecal, intracapsular, intraorbital, intracardiac, transtracheal, subcuticular, intraarticular, subcapsular, subarachnoid, intraspinal, epidural and intrasternal injection and infusion. Alternatively, other preferred routes of administration include non-parenteral routes, including topical, epidermal or mucosal routes of administration, for example, intranasally, orally, vaginally, rectally, sublingually or topically.

In certain embodiments, an AC1 inhibitor of the invention can be administered in combination with one or more additional therapeutic agents. For example, although the AC1 inhibitors disclosed herein are useful for the combined treatment of neural and non-neural (for example, inflammatory) pain, in certain circumstances it may be desirable to administer the AC1 inhibitor in combination with one or more additional analgesic agents to further inhibit pain in a mammal. Non-limiting examples of other pain-killing agents with which an AC1 inhibitor of the invention can be combined include μ opioid receptor agonists (e.g., morphine), NMDA receptor antagonists (e.g., ketamine); cycloxygenase inhibitors (e.g., Bextra™, Celebrex™), prostaglandin inhibitors (e.g., acetaminophen); antiepileptic medications (e.g., carbamazepine) and gabapentin.

In another aspect of the present invention, an article of manufacture is provided. The article of manufacture comprises packaging material containing a composition. The composition comprises an AC1 inhibitor having the general chemical formula (1) as shown above and a pharmaceutically acceptable carrier as described above. The packaging material is labeled to indicate that the composition is useful in the combined simultaneous treatment of both neural and non-neural pain.

The composition for inclusion in the article of manufacture may comprise any suitable administrable form and may also comprise any suitable dosage, as described in detail above.

The packaging material may be any suitable material generally used to package compositions used for therapy, including bottles, cartons, tubes, and the like.

Embodiments of the present invention are described in the following specific examples which are not to be construed as limiting.

EXAMPLES

Cell Culture

Human embryonic kidney 293 (HEK293; ATCC# CRL-1573) cells that are known to be deficient in AC1 were grown at 37° C. in DMEM supplemented with 10% fetal bovine serum in a humidified 95% air, 5% $CO_2$ incubator.

Expression of AC1 in HEK293 Cells

The AC1 expression vector (pcDNA3-AC1) was generously provided by Dr. Ron Taussig (University of Texas Southwestern Medical Center). For DNA transfection, HEK293 cells were plated onto 60-mm-diameter dishes (containing DMEM with 10% fetal bovine serum (Invitrogen)) at a density of $1 \times 10^6$ per plate, grown overnight and transfected with pcDNA3-AC1 (0.8 μg DNA per plate) by Lipofectamine 2000 (Invitrogen). Stable transfected clones were selected in culture media containing 0.8 mg/ml G418 and maintained in this media.

Reverse Transcriptase-PCR

Total RNA was isolated from transfected HEK293 cells using RNeasy Mini Kit (QIAGEN Inc, Canada). RT-PCR reaction was performed in a 50 μl reaction volume by QIAGEN One Step RT-PCR Kit (QIAGEN Inc, Canada), with the following amplification conditions: initial denaturation at 94° C. for 5 min, followed by 35 cycles of 94° C. for 45 s, 58° C. for 30 s, and 72° C. for 45 s, and a final 7 min extension at 72° C. The PCR primers for AC1 were as follows: Forward: 5'-TGCCTTATTTGGCCTT GTCTACC-3'.

Reverse: 5'-GACACCCGGAAAAA TATGGCTAG-3'. PCR products were electrophoresed on 1.5% agarose gel and stained by ethidium bromide.

cAMP Assay in AC1 Transfected Cells

Adenylyl cyclase activity was determined as previously described (Storm et al., 1998) using HitHunter cAMP XS Assay kit (Discoverex, Fremont, Calif.). HEK293 cells with stable AC1 expression were grown to confluency. Cells were dissociated using 0.02% EDTA in PBS. $1 \times 10^6$ cells/ml cell suspensions were prepared in the phenol red-free DMEM media, with low glucose (Gibco), 0.1% bovine serum albumin (Sigma) and 1 mM 3-isobutyl-1 methylxanthine (Sigma, St. Louis). About 20000 cells (in 20 µl) were added into each well of a 96-well culture plate. Cells were stimulated with a combination of 10 M forskolin (non-specific adenylyl cyclase activator), 10 µM A23187 (calcium ionophore) and 2 mM $CaCl_2$, in the absence or presence of potential non-competitive inhibitors of adenylyl cyclase at serial concentrations by incubating at 37° C. in a 5% $CO_2$ incubator for 45 min. cAMP XS antibody/Lysis mix (20 µl) were added and incubated for 60 minutes at RT, followed by further addition of 20 µl of cAMP XS ED reagent and incubation for 60 minutes at RT. EA/CL substrate mix (40 µl) was added and chemiluminescence was read in a CLIPR reader (Molecular Devices) after overnight incubation at RT. The assay was carried out in quadruplets.

Chemical Screening in AC1 Expressing HEK293 Cells by Dual Luciferase Reporter Assay To assess the AC1 inhibitors for their downstream effect on CREB expression, a dual luciferase reporter system was used (Williams C. Nat Rev Drug Discov. 2004 February; 3(2):125-35. Review). In this reporter assay, changes in intracellular cAMP concentration were detected as changes in expression level of firefly luciferase, the transcription of which is regulated by the transcription factor cAMP response element binding protein (CREB) binding to upstream cAMP response element (CRE). The HEK293 cells were subcultured into 96-well plates in the absence of antibiotics, grown overnight and transfected with the pGL3-CRE-firefly luciferase and pGL3-CMV-Renilla luciferase constructs (0.25 µg DNA per well) using Lipofectamine 2000 reagent. The transfected cells were incubated overnight, and media were changed to DMEM-containing 10% fetal bovine serum. After 48 h, the cells were treated independently with 10 µM forskolin, 10 µM calcium ionophore A23187 and 2 mM $CaCl_2$, or a combination of 10 µM forskolin, 10 µM A23187 and 2 mM $CaCl_2$, in the absence or presence of each AC1 inhibitor tested at a concentration of 100 µM. At the end of 6 h incubation period, cells were harvested, and luciferase activity was assayed by Dual-Luciferase Reporter Assay System (Promega). Relative light units were measured by SIRIUS luminometer.

Animals

The mice used in this work were C57B1/6 strain adults (8 weeks old) and AC1 knockout mice of C57B1/6 background (Wei et al., 2002; Neuron). The animals were housed on a 12 h: 12 h light: dark cycle with food and water available ad libidum. All the protocols were in accordance with the Animal Care Committee of the University of Toronto. Both wild type and the knockouts were well groomed. Experimenters were blind to genotype.

Formalin Lick Test for Acute Inflammatory Muscle Pain

Under brief halothane anesthesia, 10 µL of 5% formalin was injected to the left gastronemius muscle. The needle was directed from the lateral side to avoid any bony penetration and the tip was stopped at the middle of the muscle belly. The total time spent licking or biting the injected leg including the thigh and the paw was recorded and totaled every 5 minutes for a period of 2 hours. To study the effect of test compounds on behavior, each compound to be tested was injected intraperitoneally 30 minutes before the intramuscular injection of formalin.

Induction of Chronic Inflammatory Muscle Pain

A muscle model of mechanical allodynia developed originally to study chronic pain (Sluka et al., 2001) was adapted for these experiments. Mice were briefly anaesthetized under halothane. 20µ liters carrageenan (3%, in normal saline pH 7.2) was injected intramuscularly deep into the left gastronemius muscle. Normal saline was used as a control. Injections were carried out on days 1 and 5. Behavioral nociceptive responses were measured on days 1, 2, 5 (before and after injection), 14 and 28.

Responses to Innocuous Mechanical Stimuli

Mice were placed in a plexi-glass restrainer and allowed to acclimate for 30 minutes prior to testing. Mechanical allodynia was assessed based on the responsiveness of the hind paw to the application of von Frey filaments (Stoelting, Wood Dale, Ill.) to the point of bending. Positive responses include licking, biting and sudden withdrawing of the hind paw. Experiments were carried out to characterize the threshold stimulus. Mechanical pressure from 1.65 filament (force 0.008 gm) was found to be innocuous. This filament was then used to test mechanical allodynia. Ten trials were carried out each time at an interval of 5 minutes and the results were expressed as a percentage of positive responses. Positive responses included prolonged hind paw withdrawal followed by licking or scratching.

Assessment of AC1 Inhibition on Neuropathic Pain

Neuropathic pain was induced by ligating the common peroneal nerve as previously known in the art. This method was found to be an efficacious mouse model for assessing behavioral nociceptive responses in neuropathic pain. The effect of AC1 inhibition was assessed on maximal mechanical allodynia over the dorsum of the foot on the ipsilateral side of ligation on day 7. Experiments were carried out in both AC1 knockout mice as well as in normal mice 30 minutes following intraperitoneal injection of AC1 inhibitors as well as oral administration of an AC1 inhibitor.

Data Analysis

Results are expressed as mean±standard error of the mean (SEM). Statistical comparisons were performed by two-way analysis of variance (ANOVA). $P<0.05$ was considered statistically significant Chemicals The chemicals (inhibitors) tested using the tests described above include those exemplified in FIG. 6.

Results

Concentration-Dependent Effect of Chemical in AC1 Stable Expression HEK293 by cAMP Assay The AC1 expression vectors were stably transfected into HEK293 cells, and AC1 expression was confirmed by RT-PCR (FIG. 1a—Lane 1: 100 bp DNA ladder molecular weight marker. Lane 2: PCR products from AC I expression vector pcDNA3-AC1 as control. Lane 3: HEK293 transfected with vector without AC 1. Lane 4: HEK293 transfected with AC 1 expression vector. PCR products were electrophoresed on 1.5% agarose gel and stained by ethidium bromide.

Then, the stimulatory effect of forskolin and A23187 was compared in HEK293 cells with and without AC1 expression. It was found that both forskolin and A23187 could induce higher cAMP levels in AC1-expressing cells than in HEK293 cells without AC1 expression (FIG. 1b). A combination of forskolin and A23187 resulted in a higher level of cAMP (FIG. 1b). Inhibitors were then tested for their effect on forskolin and calcium ionophore-stimulated cAMP levels in AC1 transfected HEK 293 cells. All the inhibitors showed statistically significant reduction in cAMP levels (P<0.001) (FIG. 1c).

Effect of Novel AC1 Inhibitors on CREB Expression

The stimulatory effect of forskolin and A23187 on CREB expression in HEK293 cells with or without AC1 expression was compared. Both forskolin and A23187 induced stronger luciferase activity in AC1 expression cells than in HEK293 cells without AC1 expression. A combination of forskolin and A23187 could cause the most robust induction of luciferase activity. The effect of each AC1 inhibitor on AC1 stable expression HEK293 stimulated by forskolin plus A23187 was then determined. It was found that all the inhibitors tested inhibited luciferase activity at a concentration of 100 μM (FIG. 1d).

Figure 2:
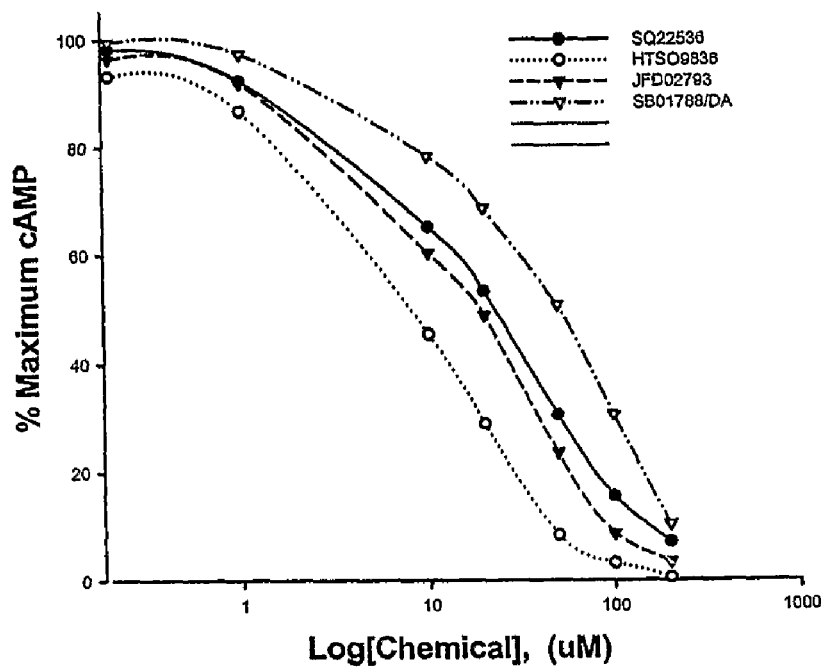
FIG. 2 is a logarithmic plot of the dose dependent inhibition of cumulative activation of AC1 expression by selected AC inhibitors.

Dose Dependent Inhibition of Cumulative Activation of AC1 Expression by Selected AC Inhibitors AC1 expressing-HEK293 cells were treated with a combination of 10 μM forskolin, 10 μM A23187 and 2 mM $CaCl_2$ in the presence of AC1 inhibitors. cAMP production was inhibited by each inhibitor in a concentration-dependent manner between 0.2 and 200 μM, with an IC50 of 22 μM for SQ22536, 10 μM for HTS09836, 18 μM for JFD02793 and 45 μM for SB01788/DA (FIG. 2).

Figure 3:
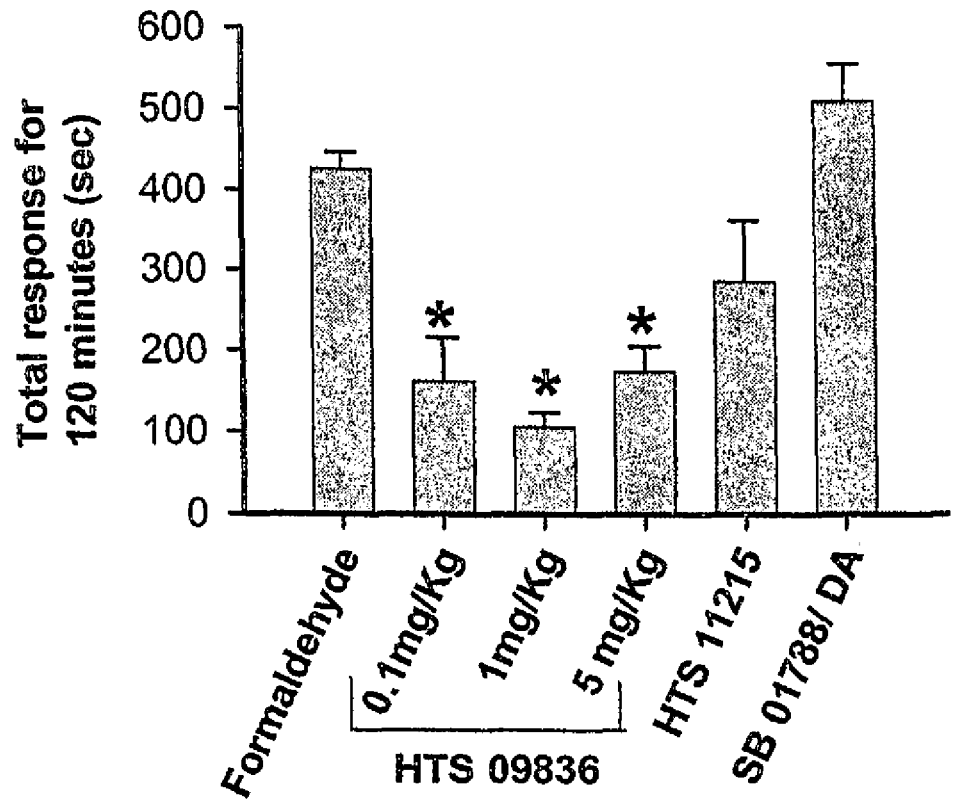
FIG. 3 is a bar graph showing dose response of the adenylyl cyclase inhibitors on acute inflammatory muscle pain.

Dose Dependent Inhibition of Nociceptive Responses in Acute Inflammatory Muscle Pain by the Novel AC1 Inhibitor HTS09836 showed significant reduction (P<0.001) of licking response of acute muscle inflammatory pain at a dose range of 0.1 to 5 mg/kg bodyweight with a peak response at 1 mg/kg body weight (FIG. 3).

Adenylyl Cyclase 1 Contributes to Acute Persistent Inflammatory Muscle Pain

Figure 4:
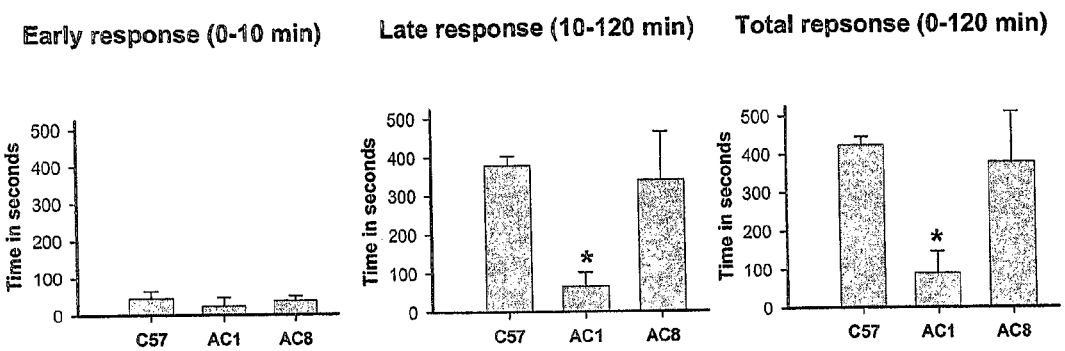
FIG. 4 illustrates by bar graph the effect of genetic deletion of calcium stimulated isoforms of adenylyl cyclases in acute persistent muscle pain induced by intramuscular formalin (a) and in neuropathic pain induced by mechanical allodynia (b)
Figure 4:
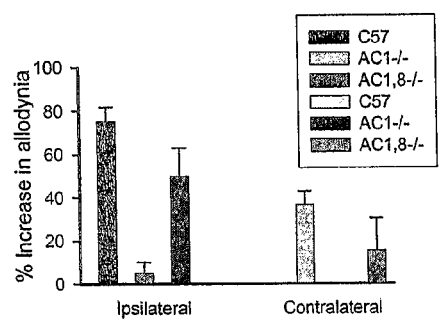

The contribution of AC1 to an animals' behavioral responses was assessed in acute muscle pain induced by intramuscular injection of 10 μl of 5% formaldehyde into the left gastronemius muscle. Care was taken to inject through a lateral approach and the needle tip was kept at the middle of the muscle. The formalin test is a common test of tissue injury-mediated inflammatory pain induced behavioral changes (Haley et al., 1990), (Wei et al., 2001; Wei et al., 2002a). Licking and biting response of the animal on the injected leg for 120 minutes was observed (wild-type, N=8 mice for saline control; wild-type, N=8 mice for formaldehyde control; injection AC1, N=8 mice) (FIG. 4a). Depending on NMDA receptors at different levels of the brain or spinal cord, formalin-induced behavioral responses consist of three phases ((Haley et al., 1990) and (Wei et al., 2001). First phase of responses were not significantly altered in AC1 knockout compared to the wild type indicating that AC1 does not significantly contribute to the early phase of the acute sensory responses to formaldehyde. A significant difference was observed between the wild type and AC1 knockout mice in phase 2 and 3 indicating that AC1 is essential for the continued responses during acute inflammation. Calmodulin-stimulated ACs are activated by NMDA receptor-mediated calcium entry and the reduction in phase 2 and 3 may be due to the loss of NMDA receptor-dependent synaptic potentiation that otherwise would have lasted several hours (Wong et al., 1999).

Adenylyl Cyclase 1 Contributes to Neuropathic Pain

Mechanical allodynia induced during neuropathic pain was tested on day 7 after ligation of the left common peroneal nerve. The behavioral responses of animals were plotted against the time during the three phases in 120 minutes. AC1 KO mice exhibited a significant reduction in responses during all the phases in the ipsilateral side.

AC1 Inhibitor Reverses Chronic Inflammatory Muscle Pain and Neuropathic Pain

Figure 5:
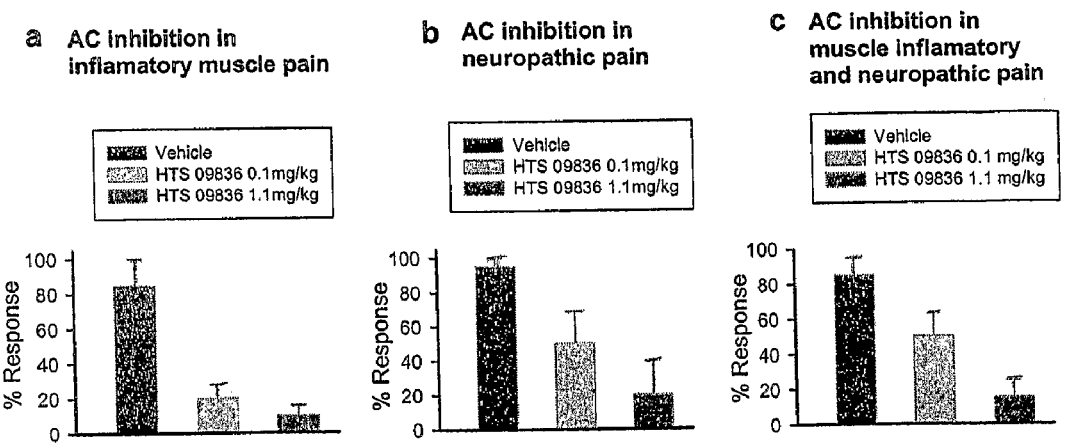
FIG. 5 illustrates by bar graph the effect of the AC1 inhibitor, HTS 09836, on chronic inflammatory muscle pain (a), on neuropathic pain (b) and on combined neuropathic and inflammatory muscle pain.
Figure 7:
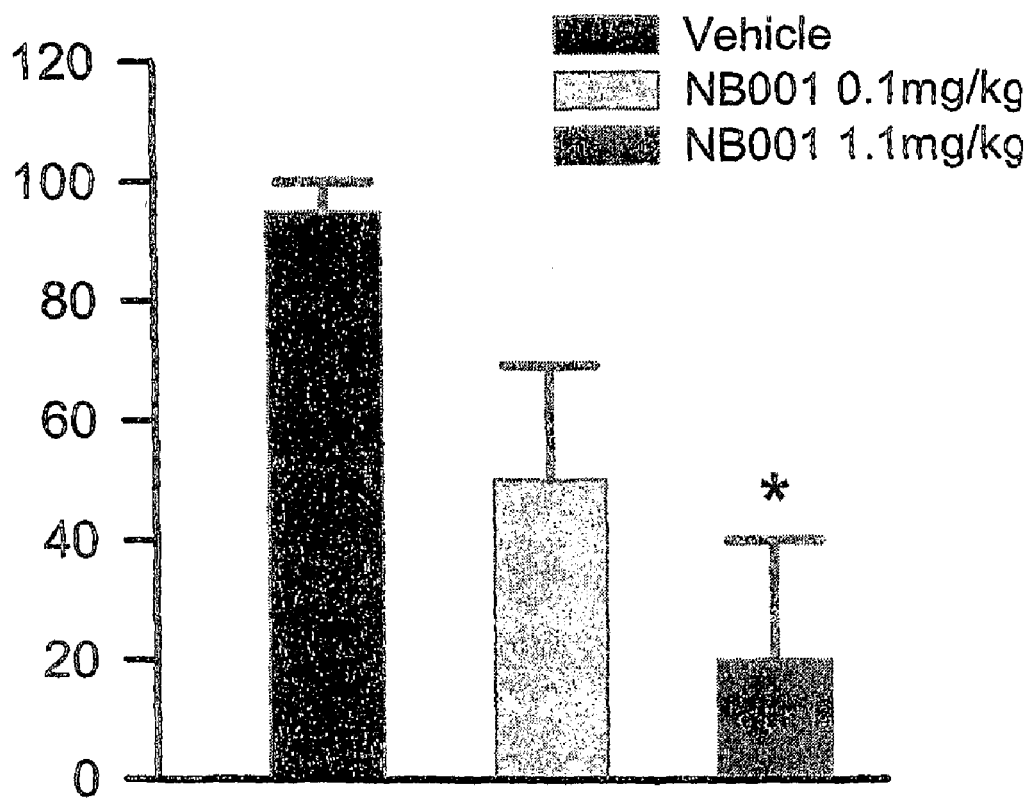
FIG. 7 graphically illustrates the inhibition of AC1 (and reduction of neuropathic pain) by i.p. administration of a compound in accordance with the invention.
Figure 8:
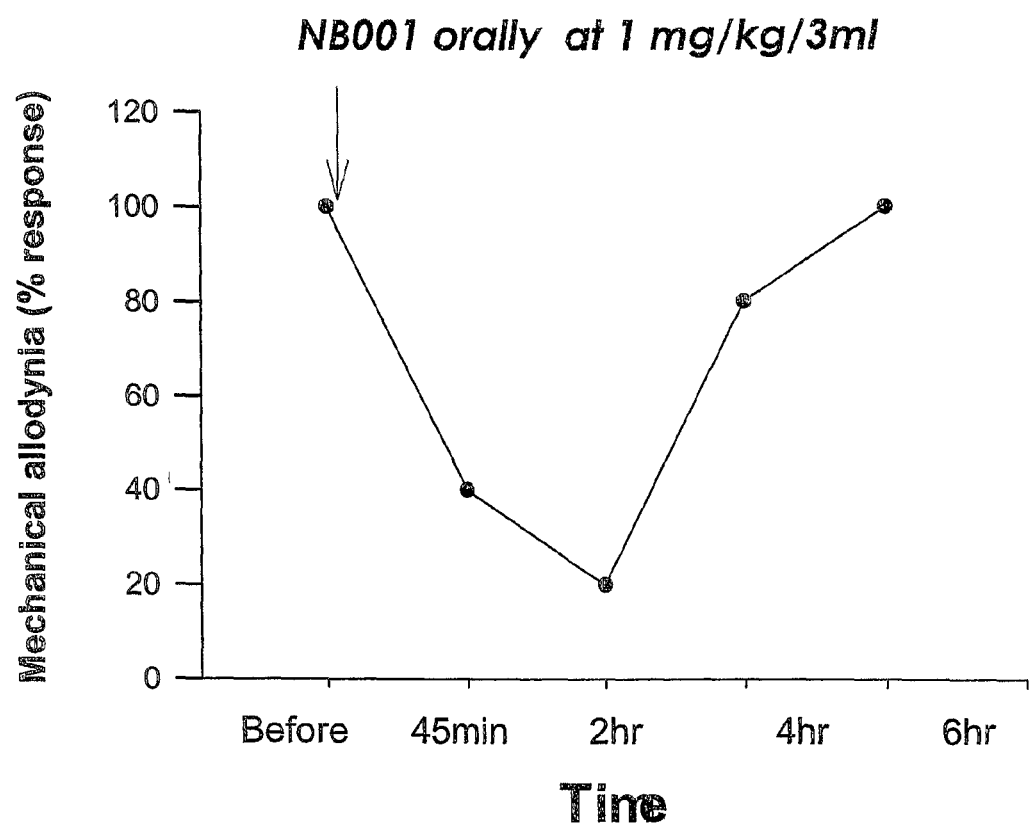
FIG. 8 illustrates the reduction of mechanical allodynia on oral administration of a compound in accordance with the invention.
Figure 9:
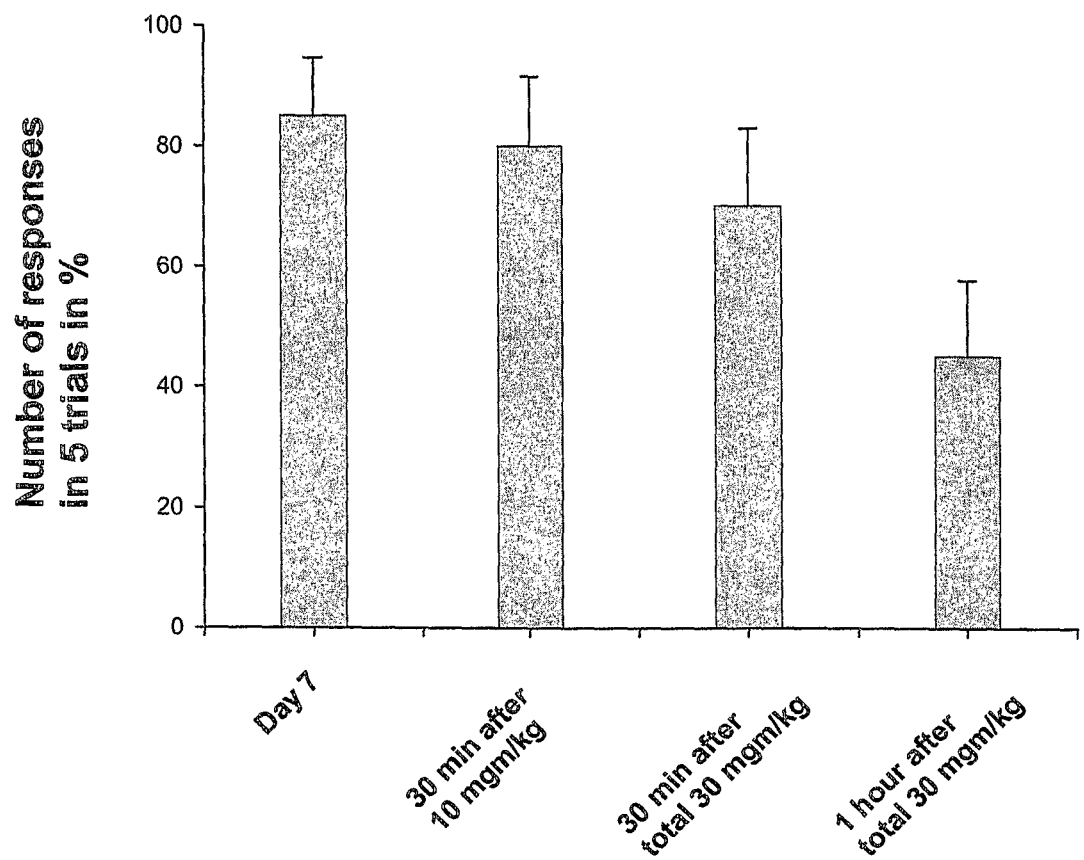
FIG. 9 illustrates the cumulative effect of gabapentin on withdrawal responses in a mouse pain model.

AC1 inhibitors were tested for anti-nociceptive effect on chronic inflammatory muscle pain. Mechanical responses to von Frey filament were tested. Dosages of both 0.1 and 1 mg/kg body weight showed significant reduction in mechanical allodynia. The dosage 1 mg/kg weight was found to have superior effect (FIG. 5a). For neuropathic pain, allodynia was significantly reduced at dosages of 0.1 and 1 mg/kg body weight (FIG. 5b). Mechanical allodynia in a more severe form of pain, introduced as a combination of chronic inflammatory pain and neuropathic pain, was significantly reduced by pre-treatment of animals (i.p. injection) with HTS 09836 both at 0.1 and 1 mg/kg body weight (FIG. 5c) and NB001 at 0.1 mg/kg and 1.1 mg/kg body weight (FIG. 7). Oral administration of 1 mg/kg/3 ml NB001 to pain model (rat) also showed a significant reduction in mechanical allodynia (FIG. 8) as compared with the response to gabapentin (FIG. 8).

Discussion

AC1 knockout mice exhibited significant reduction in phase 2 and 3 of persistent inflammatory pain sensation indicating that Ca-calmodulin stimulated ACs are key molecules in persistent muscle pain perception. Mice lacking AC1 showed reduced neuropathic pain, failed to exhibit long term hyperalgesia in chronic inflammation of both subcutaneous tissue and muscle. Since cAMP is essential for normal functions in most of the cells, non-competitive inhibitors of these enzymes were tested to select those that will inhibit AC1 specifically to minimize effect on other metabolic pathways.

Screening of these inhibitory molecules for their activity on AC1 transfected cell lines in culture permitted selection of a family of AC1 specific inhibitors. Since AC1 is neuron specific, these non-competitive inhibitors are expected to act only on neurons. Significant reduction in behavioral nociceptive responses in acute persistent, neuropathic and chronic subcutaneous and muscle inflammatory pain in animal models by AC1 selective inhibitors indicates the role of AC1 in mediating these different types of pain.

REFERENCES

Anderson L E, Seybold V S (2000) Phosphorylated cAMP response element binding protein increases in neurokinin-1 receptor-immunoreactive neurons in rat spinal cord in response to formalin-induced nociception. Neurosci Lett 283:29-32.

Haley J, Ketchum S, Dickenson A (1990) Peripheral kappa-opioid modulation of the formalin response: an electrophysiological study in the rat. Eur J Pharmacol 191:437-446.

Kandel E R (2001) The molecular biology of memory storage: a dialogue between genes and synapses. Science 294: 1030-1038.

Kawasaki Y, Kohno T, Zhuang Z Y, Brenner G J, Wang H, Van Der Meer C, Befort K, Woolf C J, Ji R R (2004) Ionotropic and metabotropic receptors, protein kinase A, protein kinase C, and Src contribute to C-fiber-induced ERK activation and cAMP response element-binding protein phosphorylation in dorsal horn neurons, leading to central sensitization. J Neurosci 24:8310-8321.

Ko S W, Vadakkan K I, Ao H, Gallitano-Mendel A, Wei F, Milbrandt J, Zhuo M (2005) Selective contribution of Egr1 (zif/268) to persistent inflammatory pain. J Pain 6:12-20.

Li X, Lighthall G, Liang D Y, Clark J D (2004) Alterations in spinal cord gene expression after hindpaw formalin injection. J Neurosci Res 78:533-541.

Nestler E J (2001) Molecular basis of long-term plasticity underlying addiction. Nat Rev Neurosci 2:119-128.
Sluka K A, Kalra A, Moore S A (2001) Unilateral intramuscular injections of AC1dic saline produce a bilateral, long-lasting hyperalgesia. Muscle Nerve 24:37-46.
Wei F, Xu Z C, Qu Z, Milbrandt J, Zhuo M (2000) Role of EGR1 in hippocampal synaptic enhancement induced by tetanic stimulation and amputation. J Cell Biol 149:1325-1334.
Wei F, Wang G D, Kerchner G A, Kim S J, Xu H M, Chen Z F, Zhuo M (2001) Genetic enhancement of inflammatory pain by forebrain NR2B overexpression. Nat Neurosci 4:164-169.
Wei F, Qiu C S, Liauw J, Robinson D A, Ho N, Chatila T, Zhuo M (2002a) Calcium calmodulin-dependent protein kinase IV is required for fear memory. Nat Neurosci 5:573-579.
Wei F, Qiu C S, Kim S J, Muglia L, Maas J W, Pineda U V, Xu H M, Chen Z F, Storm D R, Muglia L J, Zhuo M (2002b) Genetic elimination of behavioral sensitization in mice lacking calmodulin-stimulated adenylyl cyclases. Neuron 36:713-726.
Wong S T, Athos J, Figueroa X A, Pineda V V, Schaefer M L, Chavkin C C, Muglia L J, Storm D R (1999) Calcium-stimulated adenylyl cyclase activity is critical for hippocampus-dependent long-term memory and late phase LTP. Neuron 23:787-798.
Woolf C J, Salter M W (2000) Neuronal plasticity: increasing the gain in pain. Science 288:1765-1769.
Wu Z L, Thomas S A, Villacres E C, Xia Z, Simmons M L, Chavkin C, Palmiter R D, Storm D R (1995) Altered behavior and long-term potentiation in type I adenylyl cyclase mutant mice. Proc Natl Acad Sci USA 92:220-224.
Xia Z, Storm D R (1997) Calmodulin-regulated adenylyl cyclases and neuromodulation. Curr Opin Neurobiol 7:391-396.
Zhuo M (2004) Central plasticity in pathological pain. Novartis Found Symp 261:132-145; discussion 145-154.

I claim:

1. A method for treating pain in a mammal comprising the step of administering to the mammal a therapeutically effective amount of a compound having the following general formula (1):

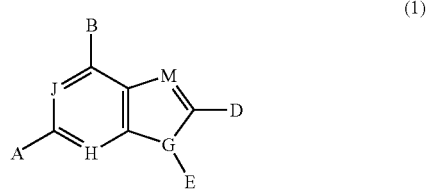

wherein:
A is H;
B is $NH_2$;
D is H;
E is —$CH_2CH_2NH(CH_2)_5OH$; and
G, H, J and M are each N.

2. The method of claim 1, wherein the pain is at least one selected from the group consisting of neural pain and non-neural pain.

3. The method of claim 1, for the combined treatment of neural and non-neural pain.

* * * * *